United States Patent

Szabo

[11] 4,087,537
[45] May 2, 1978

[54] 3-(HALOALKOXYALKYL)-CARBAMYL BENZIMIDAZOLYL CARBAMATES AND THEIR USE AS PESTICIDES

[75] Inventor: Karoly Szabo, Vienna, Austria

[73] Assignee: Syracuse University Research Corporation, Syracuse, N.Y.

[21] Appl. No.: 721,906

[22] Filed: Sep. 9, 1976

[30] Foreign Application Priority Data

Sep. 17, 1975 France .................. 75 28459

[51] Int. Cl.² .................. C07D 235/32; A61K 31/415
[52] U.S. Cl. .................. 424/273 R; 548/306
[58] Field of Search .................. 260/309.2; 424/273; 548/306

[56] References Cited

U.S. PATENT DOCUMENTS

| 3,660,421 | 5/1972 | Osieka et al. .................. 260/309.2 |
| 3,673,210 | 6/1972 | Daum et al. .................. 260/309.2 |

FOREIGN PATENT DOCUMENTS

| 1,523,597 | 3/1968 | France .................. 260/309.2 |
| 2,085,708 | 12/1971 | France. |

Primary Examiner—Natalie Trousof

Attorney, Agent, or Firm—Beveridge, DeGrandi, Kline & Lunsford

[57] ABSTRACT

Compounds of the formula:

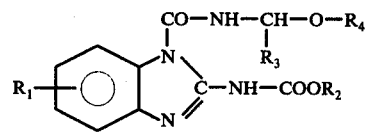

in which $R_1$ represents a hydrogen or halogen atom, an alkyl group containing from 1 to 4 carbon atoms, an alkoxy group containing 1 to 4 carbon atoms or a nitro group, $R_2$ represents an alkyl group containing from 1 to 4 carbon atoms, $R_3$ represents a hydrogen atom or an alkyl or haloalkyl group containing from 1 to 4 carbon atoms, $R_4$ represents an alkyl, haloalkyl, arylalkyl or arylhaloalkyl group containing from 1 to 12 carbon atoms, at least one of the groups $R_3$ and $R_4$ being a halogenated group.

These compounds are systemic fungicides, antisporulants and sterilizers of acaridae eggs.

15 Claims, No Drawings

3-(HALOALKOXYALKYL)-CARBAMYL BENZIMIDAZOLYL CARBAMATES AND THEIR USE AS PESTICIDES

The present invention relates to new derivatives of benzimidazole, method for their preparation and use of the compounds as pesticides.

The compounds according to the invention may be represented by the structural formula (1)

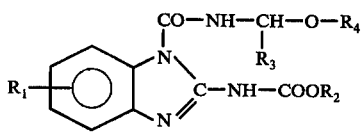

in which $R_1$ represents a hydrogen or halogen atom, an alkyl group containing from 1 to 4 carbon atoms, an alkoxy group containing from 1 to 4 carbon atoms or a nitro group, $R_2$ represents an alkyl group containing from 1 to 4 carbon atoms, $R_3$ represents a hydrogen atom or an alkyl or haloalkyl group containing from 1 to 4 carbon atoms, $R_4$ represents an alkyl, haloalkyl, arylalkyl or arylhaloalkyl group containing from 1 to 12 carbon atoms, at least one of the groups $R_3$ and $R_4$ being a halogenated group.

Included within the scope of formula 1 above are compounds wherein $R_1$ represents hydrogen or alkyl from 1 to 4 carbon atoms, $R_3$ is hydrogen or chloroalkyl containing 1 to 4 carbon atoms and $R_4$ is alkyl or chloroalkyl containing from 1 to 12 carbon atoms and particularly 1 to 4 carbon atoms.

The compounds of formula (1) may be prepared by reacting an isocyanate of the formula (2)

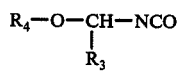

in which $R_3$ and $R_4$ have the same significance as in formula (1), with an ester of 2-benzimidazolyl-carbamic acid of formula (3)

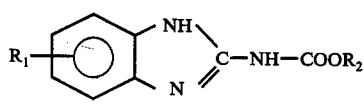

in which $R_1$ and $R_2$ have the same significance as in formula (1) according to the reaction

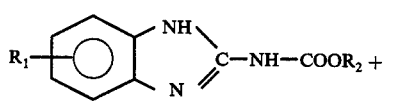

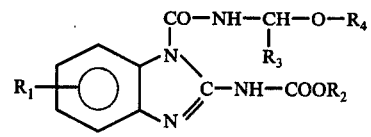

The isocyanates of formula (2) may be prepared, according to known processes, by reaction of an ether of the formula

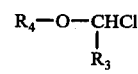

in which $R_3$ and $R_4$ have the same significance as in formula (1), with an inorganic cyanate of the formula NCO-M, in which M is a metal such as, for example, silver, sodium or potassium.

The esters of 2-benzimidazolyl-carbamic acid of formula (3) may be prepared by various known processes, in particular as described in the U.S. Pat. Nos. 2,933,504 and 3,010,968 and the disclosure of these patents is relied on and incorporated by reference for this purpose.

The reaction (A) is effected in an inert organic solvent. Suitable for this purpose are, for example, a chlorinated solvent such as methylene chloride, chloroform, carbon tetrachloride, 1,2-dichloro-ethane, an aliphatic or aromatic hydrocarbon, a carbonyl compound such as acetone or 2-butanone. Any organic solvent that is inert with respect to the reactants and reaction products may be used.

The temperature of the reaction is between −10° C and 60° C, preferably between 20° C and 40° C. Although this is not indispensable, it is also possible to operate in the presence of a catalyst known to accelerate the reaction between isocyanates and amines, for example, a tertiary amine or a tin compound; e.g. stannous octoate or dibutyltin dilaurate.

The products of the invention are shown to be systemic fungicides, antisporulants and sterilizers of acridae eggs.

The compounds of this invention enable certain parasitic fungi of cultivated plants to be combatted, and using dosages of product such that no harm is done in any way to the plant part treated, whether it be the foliage, stems, roots or seeds. That is, non-phytotoxic amounts of compounds are used. Compounds of the invention have the ability to penetrate into the treated plants by the roots, leaves, stems or seeds. Carried by the rising sap and fluids in the plant, the compounds of the invention are thus found uniformly distributed throughout the entire plant, even in the plant parts formed after the treatment. These products, called endotherapic, give to the plant a resistance against the parasitic fungi belonging to a family of well-defined species. Thus, they enable the following types of fungi to be successfully combatted: Fusarium, Botrytis, Rhizoctonia, Alternaria, Penicillium, Erysiphe, Cercospora, Ustilago, Phomopsis, Venturia, Monolia, Sclerotinia, Coccomyces, Aspergillus, Helminthosporium, Rhizopus, Colletotrichum, Verticillium, Sphaerotheca, Podosphaera and Uncinula.

The products of the invention have the original feature of enabling Ustilago maydis to be combatted by preventing this fungus from emitting the reproduction organs which are the sporodii and thus act as antisporulants.

Finally, the products of the invention, have also a very useful action on acaridae eggs which they sterilize. This characteristic is very attractive since in a single treatment one may combat two types of very different parasites.

The products according to the invention may be used alone or in admixture with other fungicidal, herbididal, insecticidal, acaricidal, bactericidal or nematicidal active materials, in all the types of formulation in use in phyto-santiary products, such as solutions in an inert organic solvent, solutions in a liquified gas inside an aerosol bomb (the said liquified gas, which is in the gaseous state at normal pressure and temperature, serving also as a propellant), suspensions in water, emulsions in water of solutions in inert organic solvent, powders for dusting, wettable powders, pastes and granules.

Examples of inert organic solvents which may be used to make solutions are, for example, aromatic or aliphatic hydrocarbons such as benzene, toluene, xylene, alkylnaphthalenes, cyclohexane, paraffins or petroleum fractions, halogenated derivatives of hydrocarbons such as chlorobenzene, chloroethylene, methylene chloride, alcohols such as butanol and glycol and their ethers and esters, ketones, dimethyl formamide, and dimethyl sulphoxide. Liquified gases which may be used as solvents are, for example, the fluorinated halogenated hydrocarbons known under the trademark "Freon".

In the solid formulations there may be incorporated finely divided inert carriers such as chalk, silica, kaolin, clay, talc or diatomaceous earth. When using emulsions and dispersions, surface active agents may be employed in order to homogenize the compositions on one hand and on the other hand to increase their wetting power on plants, their adherence and their length of persistence.

The formulations described above may contain from 0.5 to 95% by weight of products according to the invention. They may be applied to the plants, to the soil or to the seeds, by the usual methods such as dusting, coating, injection, spraying, as a mist, after possible dilution so as to obtain a desirable rate of application, e.g:

10 to 100 g of product according to the invention per hectoliter for spraying treatments.

10 to 50% by weight of product according to the invention for the treatment of the seeds.

90 to 95% kg of product according to the invention per hectoliter for applications at very low volume.

For the treatment of the soil, for example by injection, the dosage of product according to the invention used will be from 10 to 200 g per cubic meter of soil.

For the treatment of crops by spraying of the ordinary type, the dosage used will be from 100 to 1000 g of product per hectare.

Finally, for the treatment of seeds, 200 g of powder containing 10 to 50% of product per quintal of grain will generally be used.

The following examples illustrate the present invention.

EXAMPLE 1

5 liters of dry chloroform, 283 g of methyl-2-benzimidiazolyl-carbamate and 199 g of 2-chloro-ethoxy-methyl-isocyanate are introduced into a reactor. The suspension thus obtained is stirred for 24 hours at 20° C.

41 g of unreacted methyl-2-benzimidazolyl-carbamate are separated by filtration. The solution is then evaporated to dryness. The residue obtained is washed in hexane and dried, and provides 408 g (a yield of 85% with respect to the isocyanate used) of a solid product of which the analysis by infra-red spectrography (IR) and nuclear magnetic resonance spectrography (RMN) shows that it has the formula:

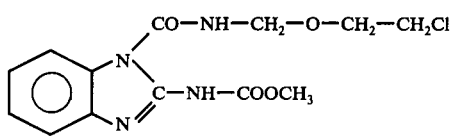

This product melts at 148° C, with incipient decomposition.

EXAMPLE 2

112 cc of dry chloroform, 4.55 g of methyl-2-benzimidazolyl-carbamate and 4.08 g of a mixture containing 30% of 2-chloro-propoxy-methyl isocyanate and 70% of 1-methyl-2-chloroethoxy-methyl-isocyanate are introduced into a reactor. After stirring for 24 hours at 20° C, the chloroform is evaporated. The residue obtained is washed with hexane and dried. 8 g of a solid product melting at 120° C are obtained, of which the analysis by IR and RMN shows that it is a mixture containing about 30% of the product of the formula:

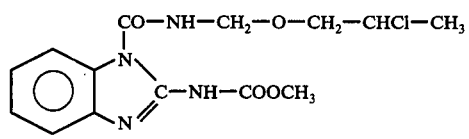

and about 70% of the product of the formula:

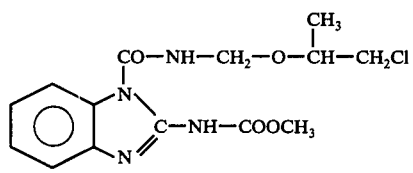

EXAMPLE 3

The following ingredients are introduced into a reactor: 120 cc of dry chloroform, 5.2 g of a mixture containing about 40% of methyl 4-methyl-2-benzimidazolyl-carbamate and about 60% of methyl 5-methyl-2-benzimidazolyl-carbamate (this mixture is obtained by applying the processes described in the patents cited on page 2 to a mixture of 70% of 3,4-diamino-toluene and 30% of 2,3-diamino-toluene), and 4.06 g of 2-chloroethoxy-methyl-isocyanate.

After stirring for 24 hours at 20° C, the reaction system is filtered and the solution obtained by filtration is evaporated to dryness. The residue is washed with hexane and dried. There is obtained 7.9 g of a solid product melting at 82° C. Analysis by IR and RMN shows that the product is a mixture containing about 40% of the compound of the formula:

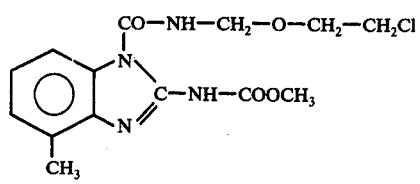

and about 60% of the compound of the formula:

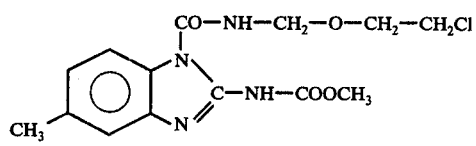

EXAMPLES 4 to 6

Following the same procedure as in the preceding examples, the products represented in the following table are prepared:

| Isocyanates used | Benzimidazolyl-carbamic esters used | Products prepared |
|---|---|---|
| 2,3-dichloro-1-methyl-propoxymethyl isocyanate $CH_2Cl—CHCl—CH(CH_3)—O—CH_2—NCO$ | methyl 2-benzimidazolyl-carbamate | benzimidazole with $CO—NH—CH_2O—CH(CH_3)—CHCl—CH_2Cl$ and $C—NH—COOCH_3$ |
| 1-methoxy-2-chloro-ethyl-isocyanate $CH_3—O—CH(CH_2Cl)—NCO$ | methyl-2-benzimidazolyl-carbamate | benzimidazole with $CO—NH—CH(OCH_3)—CH_2Cl$ and $C—NH—COOCH_3$ |
| 1-ethoxy-2-chloro-ethyl-isocyanate $CH_3CH_2—O—CH(CH_2Cl)—NCO$ | methyl-2-benzimidazolyl-carbamate | benzimidazole with $CO—NH—CH(OC_2H_5)—CH_2Cl$ and $C—NH—COOCH_3$ |

In the examples 7 to 17 which follow, the use of the invention is illustrated with respect to the fungicidal, antisporulant and sterilizing acaridae eggs activities. In these examples the dilutions of the compounds are effected with water (unless the contrary is mentioned), in the presence of a non-ionic dispersing agent at a concentration of 1%. The tests identified as control tests are made with water only containing the dispersing agent.

EXAMPLE 7

The activity of the compounds on the mycelium growth

The nutrient medium used is the Czapock medium of the following composition:

| | |
|---|---|
| Sodium nitrate | 2 g |
| Dipotassium hydrogen phosphate | 1 g |
| Potassium chloride | 0.5 g |
| Magnesium sulphate (7H$_2$O) | 0.5 g |
| Iron sulphate (7H$_2$O) | 0.01 g |
| Saccharose | 30 g |
| Gelose | 15 g |
| Water q sp | 1000 ml. |

The dilutions of the compounds according to the invention are incorporated in this medium maintained in a fused state at 45° at the rate of one part by volume to 10 parts of nutrient medium. The dilutions are such that the final concentrations of the compounds in the nutrient medium are as follows:

$C_0 = 0$ ppm (control)
$C_1 = 0.1$ ppm
$C_2 = 0.4$ ppm
$C_3 = 1.6$ ppm
$C_4 = 6.4$ ppm The medium is then run into Petri dishes of 90 mm diameter and allowed to cool and solidify. Each dish is contaminated with fragments of mycelium removed from fungus cultures aged eight days. These fungi are *fusarium roseum, rhizoctonia solani* and *phomopsis viticola.*

These dishes are incubated for 2 days in a room maintained at 22° C and at a relative atmospheric humidity of 70%. During these 2 days, the growing mycelium creates circular regions around the contamination point, the diameter of which is measured.

The results obtained with the compounds of examples 1, 2 and 3 are shown in table No. 1 below. In this table the diameters of the circular regions obtained in the dishes containing the nutrient medium treated with the compounds according to the invention are expressed as a percentage of the diameter of the circular regions obtained in the control dishes containing the untreated nutrient medium. 0% then represents a total activity, and 100% represents the state of the control; that is to say, a zero activity.

Table No. 1

| Fungus | Fusarium Roseum | | | | Phomopsis Viticola | | | | Rhizoctonia Solani | | | |
|---|---|---|---|---|---|---|---|---|---|---|---|---|
| Product | 0.1 ppm | 0.4 ppm | 1.6 ppm | 6.4 ppm | 0.1 ppm | 0.4 ppm | 1.6 ppm | 6.4 ppm | 0.1 ppm | 0.4 ppm | 1.6 ppm | 6.4 ppm |
| Product of Example | | | | | | | | | | | | |
| No. 1 | 100 | 75 | 90 | 17 | 70 | 3 | 3 | 3 | 100 | 100 | 100 | 44 |
| No. 2 | 67 | 67 | 80 | 0 | 66 | 27 | 3 | 3 | 100 | 100 | 95 | 36 |
| No. 3 | 100 | 100 | 100 | 50 | 64 | 45 | 6 | 9 | 100 | 100 | 100 | 35 |
| CONTROL | 100 | | | | 100 | | | | 100 | | | |

EFFECT ON THE MYCELIUM GROWTH — Concentration of the product

EXAMPLE 8

Inhibition action of the compounds on the germination of the spores

1st Test

The same nutrient medium as in example 7 (Czapeck medium) is used and the active material is incorporated therein in the same way.

The final concentrations of compound according to the invention in the nutrient medium are:

$C_0 = 0$ ppm (control)
$C_1 = 7.5$ ppm
$C_2 = 15.-$ ppm
$C_3 = 30.-$ ppm
$C_4 = 60.-$ ppm The medium thus treated is run into the cavities of wax plates and left to cool and solidify. The balls of nutrient medium are contaminated by deposition on each 50 μl of an aqueous suspension of spores of the species botrytis cinerea or penicillium expansum. The wax plates are put in Petri dishes 15 cm in diameter having a wet filter paper at the bottom. They are left to incubate for 24 hours at a temperature of 22° C. After which, the ungerminated spores are counted under the microscope and the number obtained is expressed as a percentage of the total number of spores counted. 0% signifies that all the spores have germinated, which is the case with the control, 100% signifies that no spores has germinated, therefore that the product has a total inhibitory action.

The results obtained with the compound of example 1 are collected in table No. II below.

Table No. II
PERCENTAGE OF UNGERMINATED SPORES — Concentration of the product

| Fungus | Botrytis Cinerea | | | | Penicillum Expansum | | | |
|---|---|---|---|---|---|---|---|---|
| Product | 7.5 ppm | 15 ppm | 30 ppm | 60 ppm | 7.5 ppm | 15 ppm | 30 ppm | 60 ppm |
| Product of Example 1 | 75 | 95 | 100 | 100 | 80 | 90 | 97.5 | 100 |
| Control | 0 | | | | 0 | | | |

Second Test

In this test, called the "MacCallan" test, 1 ml of aqueous suspension of compound is added to 1 ml of suspension of spores of *Alternaria tenuis* so as to obtain in the final mixture the following concentrations of compounds of the invention:

$C_0 = 0$ ppm (control)
$C_1 = 1.28$ ppm
$C_2 = 5.12$ ppm
$C_3 = 25.-$ ppm
$C_4 = 100.-$ ppm Drops of these mixtures are deposited in the cavities of wax plates and the plates are put in Petri dishes of 15 cm diameter, in a water saturated atmosphere. They are left to incubate for 24 hours at a temperature of 22° C. Then the percentage of ungerminated spores is determined using a microscope. 0% signifies that all the spores have germinated, 100% that no spore has germinated, therefore that the product has a total activity.

The results obtained with the compound of example 1 are tabulated in table No. III below.

Table No. III
PERCENTAGE OF UNGERMINATED SPORES — Concentration of the product

| Fungus | Alternaria Tenuis | | | |
|---|---|---|---|---|
| Product | 1.28 ppm | 5.12 ppm | 25 ppm | 100 ppm |
| Product of Example No. 1 | 12.5 | 16.5 | 16.2 | 19.5 |
| Control | 5.5 | | | |

Third Test (test by the method of inhibition zones)

A gelable nutrient medium (Czapeck medium) is made which is maintained in the fused state. In this medium are incorporated spores of the fungus penicillium expansum or *botrytris cinerea*. The contaminated medium is run into Petri dishes of 10 cm diameter where it solidifies.

Suspensions of product of various concentrations are prepared and are deposited at the rate of 10 μl on pieces of paper filter of a diameter of 0.4 cm. These pieces are placed on the surface of the medium. The product expands in the gellike medium where it prevents the germination of spores by producing around the point of application circles called "zones of inhibition". These zones are measured.

The results thus obtained with the compounds of examples 1, 2 and 3 are shown in tables 4 and 5 following hereto.

Table No. IV
DIAMETER IN CM OF THE ZONE OF INHIBITION — Dosage of Product

| Fungus | Pencillium Expansium | | | |
|---|---|---|---|---|
| Product | 0.1 μg | 0.24 μg | 0.6 μg | 1.5 μg |
| Product off Example 1 | 0.35 | 0.75 | 2.4 | 3.8 |
| Control | 0 | | | |

Table No. V
DIAMETER IN CM OF THE ZONE OF INHIBITION — Dosage of Product

| Fungus | Botrytis Cinerea | |
|---|---|---|
| Product | 0.5 μg | 1 μg |
| Product of Example 1 | 3.55 | 4.4 |
| Product of Example 2 | 2.95 | 3.65 |
| Product of Example 3 | 2.20 | 2.70 |
| Control | 0 | 0 |

EXAMPLE 9

Preventive Action of the Compounds With Regard to Barley Oidium

Water suspensions of the compounds of the following concentrations are prepared:

$C_0 = 0$ g/hl (control)
$C_1 = 0.156$ g/hl
$C_2 = 0.625$ g/hl
$C_3 = 2.5$ g/hl
$C_4 = 10.-$ g/hl These suspensions are sprayed on plants of "Rika" barley cultivated in pots of 250 ml and aged 12 days, the amount of suspension used by unit of surface of the pots being equivalent to 1000 l/ha. 24 hours after the treatment, spores of *Erysiphe graminis* are dusted on the foilage of the barley and the plants are left in a greenhouse at 22° C for 7 days.

The number of oidium spots present on the first leaf is noted. This number shows the level of contamination. The level of contamination of the treated plants is expressed as a percentage of the level of contamination of the control plants. 0% signifies that there is no contamination, 100% that the treated plants are as contaminated as the control plants.

The results obtained with the compounds of the examples 1, 2 and 3 are given in table VI below.

Table No. VI
PREVENTIVE ACTION AGAINST THE OIDIUM OF BARLEY

| Fungus | Erysiphe Graminis | | | |
|---|---|---|---|---|
| | Concentration of the product in the suspension | | | |
| Product | 1.56 ppm | 6.25 ppm | 25 ppm | 100 ppm |
| Product of Example 1 | 100 | 78 | 78 | 0 |
| Product of Example 2 | 100 | 100 | 50 | 0 |
| Product of Example 3 | 100 | 75 | 25 | 0 |
| Control | | | 100 | |

EXAMPLE 10

Study of Systemicity

A hydroponic nutrient solution is prepared (solution of Hoagland & Harnon No. 1 of pH = 6). In this solution suspensions of compounds according to the invention in a concentration of 100 ppm are dispersed.

These suspensions are put into test tubes and in each tube is placed a rooted plant of "Rika" barley aged 8 days, the roots dipping in the liquid. These plants are left for 2 days in a room maintained at a temperature of 22° C and at a relative atmospheric humidity of 70%.

Then a gelable nutrient medium Czapeck is made (see example 7) in which spores of *penicillium expansum* are incorporated at 50° C. This contaminated medium is run into Petri dishes of 9 cm diameter.

Vegetation specimens 0.5 cm in length are taken of the "Rika" barley plants and this is done at the three following levels:
Level 1 = point of the sheath
Level 2 = middle of the first leaf
Level 3 = middle of the second leaf These specimens are placed in the Petri dishes on the surface of the gel containing the spores of *penicillium expansum*. If the product is systemic, it is found in the sap exuding from the plant specimen thus placed. This sap wets the surface of the nutrient medium in which the product can migrate and inhibit the germination of the spores of *penicillium expansum*, thus forming a halo surrounding the specimen of treated plants. This halo is called the "inhibition zone".

The presence of these inhibition zones therefore enables the determination whether the product is systemic, i.e. that it penetrates into the sap system of the plant. In addition, the measure of the diameter of these zones shows that there is a relation between this diameter and the concentration of compound in the initial nutrient solution into which the roots of the barley plants have been placed. This measure is made 3 days after the deposit of the plant specimens on the medium.

The results obtained with the compounds of examples 1, 2, and 3 are tabulated in table No. VII below, in which the figures represent the diameter in cm of the inhibition zones.

Table No. VII
STUDY OF SYSTEMATICITY

| Product | Level of Samples | | |
|---|---|---|---|
| | Level 1 | Level 2 | Level 3 |
| Product of Example 1 | 4.12 | 4.50 | 3.70 |
| Product of Example 2 | 3.40 | 4.90 | 3.90 |
| Product of Example 3 | 2.20 | 0.50 | 2.80 |
| Control | 0 | 0 | 0 |

EXAMPLE 11

Activity of the Compounds Against Erysiphe Graminls, by Treatment of the Soil

Aqueous suspensions of the product of the following concentrations are made:

$C_0 = 0$ ppm (control)
$C_1 = 6.4$ ppm
$C_2 = 16$ ppm
$C_3 = 40$ ppm
$C_4 = 100$ ppm Plants of "Rika" barley are cultivated in pots of 250 ml. The plants being 8 days old, the soil contained in the pots is treated with 5 ml of aqueous suspension of the product. 24 hours after the treatment spores of *Erysiphe graminis,* the reproduction organ of oidium, are dusted on the barely plants. Six days after this operation the spots of oidium present on the first leaf of the plants are counted. The number obtained is a measure of the level of contamination. The level of contamination of the treated plants is expressed as a percentage of the level of contamination of the control plants. 0% signifies that the contamination is absent, 100% that the plant is as contaminated as the control plants.

The results obtained with the compound of example 1 are shown in table No. VIII below. These results show that the product inoculated into the treated soil is absorbed by the plant by way of the roots and passes into the flow of sap, thus conferring on the plant a resistance to *Erysiphe graminis* indicating that the product is endotherapic.

Table No. VIII
ACTIVITY AGAINST THE OIDIUM OF BARLEY BY TREATMENT OF THE SOIL

| Fungus | Erysiphe Graminis | | | |
|---|---|---|---|---|
| Concentration of the product in the suspension | 6.4 ppm | 16 ppm | 40 ppm | 100 ppm |
| Product of Example 1 | 99.6 | 87 | 57 | 64 |
| Control | | | 100 | |

EXAMPLE 12

Activity of the Compounds Against *Erysiphe Graminis,* by Treatment of the Seeds In this example, the active substance is formulated in the form of powder for dusting, the carrier being talc.

The concentrations of product in the powders are the following:

$C_0 = 0$ (control)
$C_1 = 0.78\%$
$C_2 = 3.12\%$
$C_3 = 12.5\%$
$C_4 = 50\%$

The lots of seed of "Rika" barley are treated with the powders at the rate of 200 g of powder per quintal of grain and they are stirred for one and a half hours. These treated grains are sown in pots of 250 ml and these are placed in a greenhouse. Eight days after, the grown plants are contaminated by dusting with spores of *Erysiphe graminis*. After 6 days of incubation, the spots of oidium present on the first leaf of each plant are counted. The level of contamination of the plants, the seed of which has been treated, is expressed as a percentage of the level of contamination of the untreated control plants. 0% signifies that the plant has no spot of oidium, 100% that the plant is as contaminated as the control plants.

The results relative to the compound of example 1 are tabulated in table No. IX. These results show that the product coating the seeds penetrates into the sprot or germ, is carried by the sap, and confers on the plant a resistance to *Erysiphe graminis*.

Table No. IX

| Fungus | Concentration of product in the powder Erysiphe Graminis | | | |
|---|---|---|---|---|
| Product | 0.78% | 3.12% | 12.5% | 50% |
| Product of Example No. 1 | 100 | 82 | 40 | 0 |

EXAMPLE 13

Action of the Compounds Against The Cercosporiosis of the Sugar-beet

Aqueous suspensions of compounds are prepared which are applied at the rate of 1000 l/ha. The concentration of the compound in the suspension is calculated so as to use the following dosages of compound:

$D_0 = 0$ g/ha (control)
$D_1 = 150$ g/ha
$D_2 = 300$ g/ha

The plants treated are ceres monogerm sugar-beet aged two months and cultivated in the open fields.

24 hours after the treatment, the beets are contaminated by spraying them with a suspension of spores of *Cercospora beticola* containing 30,000 spores/ml. 25 days after this contamination, the spots present on 5 leaves taken at random in each lot are counted and from this the average number of spots per leaf is calculated. The value 0 indicates that the product has been completely active and fully prevented the infection by the fungus.

The results obtained with the compound of example 1 are shown in table No. X below:

Table No. X

| ACTION ON CERCOSPORIOSIS OF BEET Average number of spots of cercosporiosis per leaf Dose of product | | |
|---|---|---|
| Fungus | Cercospora Beticola | |
| Product | 150 g/ha | 300 g/ha |
| Product of example 1 | 2,7 | 0 |
| Control | 227.5 | 227.5 |

EXAMPLE 14

Action of the Compounds on the Germination of the Spores of *Ustilago Maydis*

The compounds are diluted with water and to 1 ml of these dilutions is added 1 ml of a suspension of spores of Ustilago maydis. The dilutions are calculated so as to obtain the following concentrations of the test product:

$C_0 = 0.$ ppm (control)
$C_1 = 0.8$ ppm
$C_2 = 3.1$ ppm
$C_3 = 12.5$ ppm
$C_4 = 50.$- ppm One drop of these treated suspensions is placed in the cavities of wax plates, which plates are then put in Petri dishes of 15 cm diameter, the bottom of which is provided with a moist filter paper. The whole is stored for 24 hours at 22° C. Then the number of sporidii emitted per germinated spore is counted under the microscope. The results obtained with the samples treated with the compounds of the invention are compared wtih the results obtained with the control samples. The results are expressed as a percentage of inhibition of the production of sporidii. 0% signifies that there is no inhibition, i.e. that the number of sporidii emitted is the same as for the control samples, 100% signifies that the spores treated emit no sporidii.

The results obtained with the product of example 1 are shown in the table No. XI below:

Table No. XI

| ACTION ON THE SPORULATION OF USTILAGO MAYDIS Inhibition of production of the sporidii as a percentage with respect to the untreated control | | | | |
|---|---|---|---|---|
| Fungus | Concentration Ustilago Maydis | | | |
| Product | 0.8 ppm | 3.1 ppm | 12.5 ppm | 50 ppm |
| Product of Example 1 | 95 | 100 | 100 | 100 |
| Control | | 0 | | |

EXAMPLE 15

Action of the Compounds Against *Botrytis Cinerea* on Grapes

Lots of 50 grapes (Graisse variety) are treated by soaking in aqueous dispersions of the product. The grapes are then contaminated by means of a drop of a conidium suspension applied to the opening made during the tearing away from the pedicle. 7 days after the contamination the grapes are examined and to each grape is allotted a mark according to the following scale of evaluation:

0: healthy grape
1: slight browning around the inoculum
2: browning of ¼ of the grape
3: browning of ½ of the grape
4: browning of ¾ of the grape
5: total browning of the grape The results relative to the compound of example 1 are given in the table XII below:

| Product | Concentration of the product in the Dispersion (in g/hl) | Total Rating per lot | Average rating per grape |
|---|---|---|---|
| Product of Example 1 | 30 | 133 | 2.66 |
| Control | | 210 | 4.20 |

EXAMPLE 16

Action of the Compounds on Acaridae Eggs

The products are diluted in water so as to obtain the following concentrations:

$C_0$ = 0 ppm (control)
$C_1$ = 31.2 ppm
$C_2$ = 125.- ppm
$C_3$ = 500.- ppm

Bean plants aged 15 days having two spread out cotyledonous leaves are contaminated with females of *Tetranychus urticae.* 15 females are put on each leaf. 24 hours later, these adult females mites are removed and only the eggs laid remain on the leaves.

These beans are treated by springing, on the upper and under sides of the leaves, the dilutions indicated above. Spraying is continued until the spray starts to run down the leaf.

15 days after the treatment, the living acaridae present on the beans are counted. The difference between the number of mites found on the control plants and on the treated plants represents the reduction of the population due to the ovicidal activity of the test material. This reduction is expressed as a percentage of the total population of the control. 0% signifies that there is no activity, 100% that the activity is complete.

The results obtained with the product of example 1 are collected in table No. XIII below:

Table No. XIII.

| | REDUCTION OF MOBILE POPULATION AS A PERCENTAGE OF THE POPULATION OF THE CONTROL | | |
|---|---|---|---|
| Insect | Tetranychus Urticase | | |
| Concentration of the product in the dilution | 31.2 ppm | 125 ppm | 500 ppm |
| Product of Example 1 | 7.9 | 51.5 | 93 |

EXAMPLE 17

Action of Compounds on *Venturia Inaequalis,* Agent of the Speckling of the Apple Tree The compounds are diluted with water so as to obtain a concentration of 30 g/hl.

These suspensions are sprayed on white Calville apple trees at the rate of one spray for each of 15 days. 45 days after the first treatment the level of contamination is evaluated by counting the spotted leaves. The results are expressed as a percentage of reduction of the level of contamination with respect to the level of the control. 0% signifies that the level of contamination is the same as that of the control, 100% that the product is very effective and that the level of contamination is nil.

The results obtained with the product of example 1 are given in table No. XIV below:

Table No. XIV

| Product | Concentration in g/hl | Percentage of reduction |
|---|---|---|
| Product of example 1 | 30 | 84 |

I claim:
1. A compound of the formula:

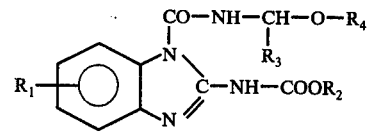

in which $R_1$ represents hydrogen or halogen, alkyl containing from 1 to 4 carbon atoms, alkoxy containing 1 to 4 carbon atoms or nitro;

$R_2$ represents alkyl containing from 1 to 4 carbon atoms;

$R_3$ represents hydrogen, alkyl or haloalkyl containing from 1 to 4 carbon atoms;

$R_4$ represents alkyl, haloalkyl, arylalkyl or arylhaloalkyl containing from 1 to 12 carbon atoms;

one at least of the groups $R_3$ and $R_4$ being a halogenated group.

2. A compound as defined in claim 1 wherein $R_1$ is hydrogen or alkyl from 1 to 4 carbon atoms, $R_3$ is hydrogen or chloroalkyl containing 1 to 4 carbon atoms and $R_4$ is alkyl or chloroalkyl containing 1 to 12 carbon atoms.

3. A compound as defined in claim 2 wherein $R_4$ is alkyl or chloroalkyl containing 1 to 4 carbon atoms.

4. A compound according to claim 3 wherein such compound is 2-methoxycarbonylamino-3-[(2-chloroethoxy)methyl]carbamyl benzimidazole of the formula:

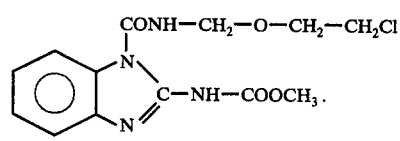

5. A compound according to claim 3 wherein such compound is a mixture of 2-methoxycarbonylamino-3-[(2-chloropropoxy)methyl]carbamyl benzimidazole of the formula:

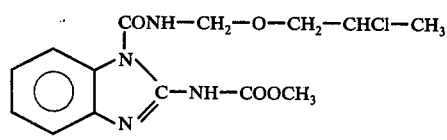

and 2-methoxycarbonylamino-3-[(2-chloro-1-methylethoxy)]carbamyl benzimidazole of the formula:

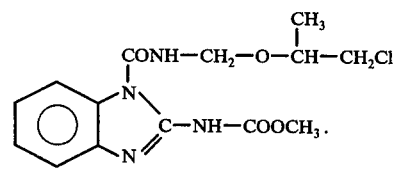

6. A compound according to claim 3 wherein such compound is a mixture of 2-methoxycarbonylamino-3-[(2-chloroethoxy) methyl]carbamyl-7-methyl benzimidazole of the formula:

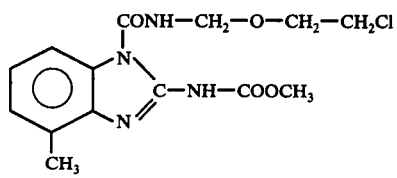

and 2-methoxycarbonylamino-3-[(2-chloroethoxy)methyl]carbamyl-6-methyl benzimidazole of the formula:

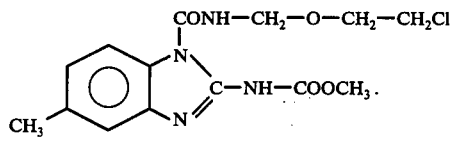

7. A compound according to claim 3 wherein such compound is 2-methoxycarbonylamino-3-[(2,3-dichloro-1-methyl-propoxy)methyl]carbamyl benzimidazole of the formula:

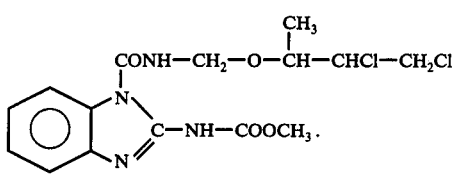

8. A compound according to claim 3 wherein such compound is 2-methoxycarbonylamino-3-[(2-chloro-1-methoxy)ethyl]carbamyl benzimidazole of the formula:

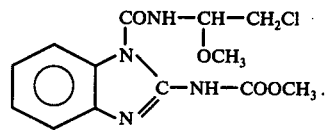

9. A compound according to claim 3 wherein such compound is 2-methoxycarbonylamino-3-[(2-chloro-1-ethoxy)ethyl]carbamyl benzimidazole of the formula:

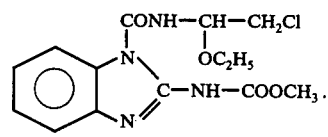

10. A method for treating a plant to control parasitic fungi comprising contacting said plant with a compound defined in claim 1 in a non-phytotoxic, fungicidally effective amount.

11. A method for treating a plant to control parasitic fungi comprising applying to the soil adjacent the plant a non-phytotoxic, fungicidally effective amount of a compound defined in claim 1.

12. A method for treating a fungus to prevent said fungus from emitting spores comprising contacting said fungus with an effective amount of a compound as defined in claim 1.

13. A method for sterilizing acaridae eggs comprising treating said eggs with a compound as defined in claim 1.

14. A method for treating seeds comprising applying to the seed an effective amount of a compound as defined in claim 1 whereby the plant which is produced upon germination of the seed has resistance to attack by fungi.

15. A composition for preventing fungi from emitting spores, for sterilizing acaridae eggs or for use as a systemic fungicide comprising 0.5 to 95% by weight of a compound defined in claim 1 and an inert vehicle or carrier therefor.

* * * * *